US008967691B2

(12) United States Patent
Mueller et al.

(10) Patent No.: US 8,967,691 B2
(45) Date of Patent: Mar. 3, 2015

(54) CHUTE ARRANGEMENT WITH STRIP-OFF FEATURE (71) Applicant: Beckman Coulter, Inc., Brea, CA (US)

(72) Inventors: Martin Mueller, Schliersee-Neuhaus (DE); Lukas Bearden, Indianapolis, IN (US)

(73) Assignee: Beckman Coulter, Inc., Brea, CA (US)

( * ) Notice: Subject to any disclaimer, the term of this patent is extended or adjusted under 35 U.S.C. 154(b) by 0 days.

(21) Appl. No.: 14/055,601

(22) Filed: Oct. 16, 2013

(65) Prior Publication Data

US 2014/0105719 A1 Apr. 17, 2014

Related U.S. Application Data (60) Provisional application No. 61/790,446, filed on Mar. 15, 2013, provisional application No. 61/714,656, filed on Oct. 16, 2012.

(51) Int. Cl.
B66C 1/42 (2006.01)
B25J 15/10 (2006.01)
B65G 11/02 (2006.01)
A61B 19/02 (2006.01)
G01F 23/00 (2006.01)
B25J 15/04 (2006.01)
(Continued)

(52) U.S. Cl.
CPC ............. *B25J 15/103* (2013.01); *B65G 11/023* (2013.01); *A61B 19/0287* (2013.01); *G01F 23/0061* (2013.01); *B25J 15/0475* (2013.01); *B65B 69/00* (2013.01); *G01F 23/2962* (2013.01); *G01N 35/00732* (2013.01); *G01N 35/0099* (2013.01); *G01S 15/04* (2013.01)
USPC .......................................... 294/86.4; 193/2 R (58) Field of Classification Search
USPC .......... 193/2 R, 4, 28, 2 A; 198/468.8, 468.2; 294/86.4; 221/210, 220, 102; 422/63, 422/65; 436/47, 48
See application file for complete search history.

(56) References Cited

U.S. PATENT DOCUMENTS 1,010,320 A * 11/1911 Ruehs ........................... 221/310
4,336,872 A * 6/1982 Noda et al. .................... 193/2 R
(Continued)

FOREIGN PATENT DOCUMENTS

DE 34 20 857 A1 12/1985
GB 2 147 268 A 5/1985
(Continued)

OTHER PUBLICATIONS

Anonymous; "Workpiece Gripper,", *IBM Technical Disclosure Bulletin*; Jun. 1, 1985; vol. 28; No. 1; pp. 327-328.
(Continued)

Primary Examiner — Saul Rodriguez
Assistant Examiner — Gabriela Puig
(74) Attorney, Agent, or Firm — Kilpatrick Townsend & Stockton LLP (57) ABSTRACT Embodiments of the invention provide systems and methods for a chute arrangement comprising an element for objects, such as, test tubes, caps, etc. released by a gripper unit such that the released objects may be collected in a container. The element may comprise a plurality of slots for a plurality of gripper fingers in the gripper unit to pass through. The element may be configured to restrain the object as the plurality of gripper fingers release the object.

20 Claims, 10 Drawing Sheets (51) Int. Cl.
*B65B 69/00* (2006.01)
*G01F 23/296* (2006.01)
*G01N 35/00* (2006.01)
*G01S 15/04* (2006.01)

(56) References Cited

U.S. PATENT DOCUMENTS

| | | | |
|---|---|---|---|
| 4,645,407 | A | 2/1987 | Williams |
| 4,676,541 | A | 6/1987 | Lord et al. |
| 5,171,979 | A | 12/1992 | Kwa et al. |
| 5,350,564 | A * | 9/1994 | Mazza et al. ............ 422/63 |
| 5,455,006 | A | 10/1995 | Aota et al. |
| 5,918,739 | A | 7/1999 | Bilof et al. |
| 5,941,366 | A | 8/1999 | Quinlan et al. |
| 6,257,091 | B1 | 7/2001 | Cohen et al. |
| 6,293,750 | B1 | 9/2001 | Cohen et al. |
| 6,498,037 | B1 * | 12/2002 | Carey et al. ............ 436/50 |
| 6,539,334 | B1 | 3/2003 | Sawafta |
| 6,859,271 | B1 | 2/2005 | Carney et al. |
| 7,402,281 | B2 * | 7/2008 | Huynh-Ba et al. ......... 422/63 |
| 7,473,897 | B2 | 1/2009 | Braendle et al. |
| 7,688,448 | B2 | 3/2010 | Bamberg et al. |
| 8,267,451 | B2 | 9/2012 | Pedrazzini |
| 2007/0080223 | A1 | 4/2007 | Japuntich |
| 2007/0258858 | A1 | 11/2007 | Rasnow et al. |
| 2007/0289660 | A1 | 12/2007 | Aylward |
| 2008/0047369 | A1 | 2/2008 | Tsujimura et al. |
| 2008/0122155 | A1 | 5/2008 | Wieland |
| 2008/0286082 | A1 | 11/2008 | Moran et al. |
| 2008/0318323 | A1 * | 12/2008 | Shintani et al. ............ 436/47 |
| 2009/0047179 | A1 | 2/2009 | Ping et al. |
| 2010/0066109 | A1 | 3/2010 | Pedrazzini |
| 2010/0101317 | A1 | 4/2010 | Ashrafzadeh et al. |
| 2010/0111384 | A1 | 5/2010 | Nagai et al. |
| 2010/0261595 | A1 | 10/2010 | Schaefer et al. |
| 2011/0065193 | A1 | 3/2011 | Kitagawa et al. |
| 2011/0089709 | A1 | 4/2011 | Neeper |
| 2011/0262896 | A1 | 10/2011 | Blecka et al. |
| 2012/0013889 | A1 | 1/2012 | Heise |
| 2012/0058900 | A1 | 3/2012 | Gisler et al. |
| 2013/0149079 | A1 | 6/2013 | Ohiso et al. |
| 2014/0036276 | A1 * | 2/2014 | Gross et al. ............ 356/614 |

FOREIGN PATENT DOCUMENTS

| | | |
|---|---|---|
| WO | 00/38046 A1 | 6/2000 |
| WO | 2006/075201 A1 | 7/2006 |
| WO | 2012/029834 A1 | 3/2012 |

OTHER PUBLICATIONS

Dukhyun, Kang et al.; "Shape Recognition by Random Grasping,"; *Proceedings of the 1992 IEEE/RSJ International Conference on Intelligent Robots and Systems*; Jul. 7-10, 1992, Raleigh NC; pp. 387-392.

Notash, Leila et al.; "Kinematic Calibration of Parallel Manipulators,"; *IEEE International Conference on Intelligent Systems for the 21st Century*; Oct. 22-25, 1995, Vancouver, BC, Canada; pp. 3310-3315.

International Search Report and Written Opinion mailed on Dec. 6, 2013 for PCT Patent Application No. PCT/US2013/053848, 15 pages.

International Search Report and Written Opinion mailed on Feb. 26, 2014 for PCT Patent Application No. PCT/US2013/065216, 11 pages.

International Search Report and Written Opinion mailed on Feb. 26, 2014 for PCT Patent Application No. PCT/US2013/065255, 11 pages.

International Search Report and Written Opinion mailed on Mar. 27, 2014 for PCT Patent Application No. PCT/US2013/065213, 11 pages.

International Search Report and Written Opinion mailed on Mar. 17, 2014 for PCT Patent Application No. PCt/US2013/065280, 14 pages.

* cited by examiner

CHUTE ARRANGEMENT WITH STRIP-OFF FEATURE

CROSS-REFERENCES TO RELATED APPLICATIONS

This application claims priority to U.S. Provisional Application No. 61/790,446 filed Mar. 15, 2013 and entitled "Specimen Gripper." This application further claims priority to U.S. Provisional Application No. 61/714,656 filed Oct. 16, 2012 and entitled "Specimen Gripper." All of these applications are herein incorporated by reference in their entirety for all purposes.

BACKGROUND

Conventional medical laboratory systems contain many components for processing patient samples, some of which are automated and some of which require manual operation. Laboratory systems today have become more efficient due to those automated components. However, there are still several components of medical laboratory systems that can be automated in order to reduce the time it takes to analyze a sample, the reliance on human intervention, and the space required to house such systems.

Some automated components of a laboratory system include a robotic arm and a specimen gripper. A conventional robotic arm in a laboratory system may be capable of moving in an x, y, or z direction. It may carry a specimen gripper with gripper fingers. The specimen gripper may grip and transport objects such as sample tubes or centrifuge buckets. A specimen gripper and robotic arm may also be used to grip and transport waste objects to discard them into a waste container. However, in some cases, when the specimen gripper releases the waste object into the waste container, the waste object may get stuck to the specimen gripper and may not separate from the specimen gripper. For example, there may be contamination on the outside surface of the waste object (e.g., from a prior aliquotting process) that may cause the object to stick to the gripper fingers. In another example, a label on the waste object may have come off or the glue from the label may have caused the object to be stuck to the gripper fingers during the waste disposal process. In such cases, human intervention may be required to remove the waste object from the gripper. This causes processing delays and requires a human being to correct the problem. Furthermore, in this process, contamination may be transported with the gripper fingers from one waste object to another, thus further increasing the likelihood of spreading the contamination.

Embodiments of the invention address these and other problems, individually and collectively.

BRIEF SUMMARY

Embodiments of the invention relate to systems and methods for a chute arrangement comprising a strip-off feature for objects, such as test tubes, caps, and the like. When objects are released by a robot gripper, the released objects may be collected in a waste container.

One embodiment is directed to an element useful for releasing an object gripped by a gripper unit, wherein said gripper unit includes a plurality of gripper fingers for gripping the object. The element comprises a tubular body comprising a central axial bore running the length of the tubular body with a first end and a second end. The tubular body is configured to receive at least a portion of said object into said central axial bore through said first end, the first end including a plurality of slots parallel to the axis of the central axial bore and being open at the first end, said plurality of slots being positioned to receive portions of the plurality of gripper fingers of the gripper unit. The said tubular body is configured to restrain the object as the plurality of gripper fingers are extracted through the plurality of slots to release the object.

One embodiment is directed to a chute arrangement for guiding an object. The chute arrangement comprises an element, an adapter unit and a bottom chute. The element comprises a tubular body comprising a central axial bore, a first end and a second end opposite to the first end, the first end comprising a plurality of slots parallel to a longitudinal axis of the central axial bore. The bottom chute is coupled to the element through the adapter unit, wherein one end of the adapter unit is coupled to the second end of the element and another end of the adapter unit is coupled to the bottom chute.

Another embodiment is directed to a method of releasing an object through a chute arrangement. The method comprises gripping the object using a plurality of gripper fingers in a gripper unit and inserting the object into the chute arrangement by means of the gripper unit. The chute arrangement comprises an element comprising an element body comprising a central axial bore, a first end and a second end, the first end comprising a plurality of slots. The method further comprises releasing the object by the plurality of gripper fingers by causing the gripper fingers to extend outward through the plurality of slots while the object is within the element of the chute arrangement.

These and other embodiments of the technology are described in further detail below.

BRIEF DESCRIPTION OF THE DRAWINGS

A further understanding of the nature and advantages of the different embodiments may be realized by reference to the following drawings.

DETAILED DESCRIPTION

Specimen containers such as sample tubes may be used to hold specimens for medical analysis. Examples of such specimens include blood, serum, gel, plasma, etc. After the specimen has been processed or after the storage period of the specimen container has expired, the specimen container may need to be discarded. Robotic gripper units may be used to grip and transport waste specimen containers for discarding them into a waste container. However, in some cases, when the gripper unit releases the specimen container into the waste container, the specimen container may get stuck to the gripper unit and may not be automatically released. For example, the outside surface of the specimen container may be sticky due to contamination, glue from a label stuck to the specimen container, etc. In such cases, human intervention may be required to remove the specimen container to minimize the processing delays. Furthermore, contamination may be transported with the gripper fingers from one specimen container to another, thus further spreading the contamination.

Embodiments of the invention provide systems and methods for a chute arrangement comprising an element for objects, such as, test tubes, caps, etc. released by a gripper unit such that the released objects may be collected in a container. Embodiments may be used for any objects that need to be collected in a container, such as specimen containers, secondary tubes that need not be stored, caps, capillary waste, pipette waste, etc.

In embodiments of the invention, at least one gripper finger in a plurality of gripper fingers may separate (e.g., strip off) from a sticky object so that the at least one gripper finger is not stuck to the object and the object is released from the gripper finger. An element can be used to surround the object to restrain (hold back) the object as the gripper fingers release the object.

An element according to an embodiment of the invention may include a hollow tubular body comprising a first end and a second end. The first end of the body may include a plurality of slots to enable a plurality of gripper fingers gripping an object surrounded by the body of the element to strip off from the object through the plurality of slots. The body of the element may have a square profile, a cylindrical profile or any suitable profile, which can accommodate an object that needs to be discarded, e.g., a specimen container, a cap, etc. The first end of the body may be open and integrated with an open end of each slot in a plurality of slots. In some embodiments, a second end of the body may be coupled to another device or unit. An element may also operate as a chute for directing a specimen container towards a container. In embodiments of the invention, the terms "stripping element", "strip-off element" and "top chute" may be used interchangeably.

A "central axial bore" may include an opening along an axis of a body. A central axial bore may be defined by a body with any suitable shape and may be of any suitable length. For example, the body defining the central axial bore may have a volume slightly larger than the volume of an object with any suitable profile (square, cylindrical, etc.) and may have a length slightly longer than the object.

In one embodiment of the invention, an element body comprising a central axial bore may be configured to surround an object, e.g., a specimen container, within the central axial bore. For example, if the specimen container is a sample tube, the diameter of the bore may be large enough to accommodate a sample tube held by a plurality of gripper fingers within the bore. In embodiments of the invention, the central axial bore may include any hollow cylindrical forms including square shaped forms.

A "slot" may include a narrow opening. A slot may have any suitable length. In some embodiments, a slot may be sized so that it is slightly wider than a gripper finger or a jaw attached to the gripper finger. The slot may also have any suitable shape including a rectangular shape. In one embodiment, a slot may be elongated, arranged axially parallel to an axis of the element body and may be open at the first end of the element.

In embodiments of the invention, a plurality of slots may be integrated in the body of an element. The number of slots in the plurality of slots may be equal to the number of gripper fingers gripping an object surrounded by the body of the element. There may be two, three, four or a suitable number of slots in the plurality of slots to allow each gripper finger in the plurality of gripper fingers to grip the object through a slot. In one embodiment, plurality of slots includes at least two slots. In one embodiment, plurality of slots includes exactly four slots. Each of the plurality of slots (e.g., four slots) may have a rectangular shape with a length smaller than a length of the body of the element and a width large enough to allow a gripper finger to move easily in and out of the slot. In one embodiment, the length of the element may be five inches, whereas, the length of each slot in the plurality of slots may be three inches, and the width of each slot may be equal to or less than about one half inch.

A gripper unit according to an embodiment of the invention may utilize plurality of gripper fingers to grip an object. The plurality of gripper fingers may comprise two or more (e.g., three, four or any suitable number) gripper fingers. In a preferred embodiment, the plurality of gripper fingers comprises four gripper fingers. Each gripper finger may take a form of an elongated structure that is capable of gripping an object such as a sample tube in collaboration with one or more other gripper fingers. In some embodiments, an exemplary gripper finger may have a rectangular, axial and/or longitudinal, cross-section with predetermined thickness (e.g., one quarter of an inch or more) and length (e.g., three inches or more). Suitable gripper fingers may be rigid or may have one or more pivoting regions.

In some embodiments, a jaw may be coupled to one end (gripping end) of the gripper finger to aid in gripping the object. The other end of the gripper finger may be coupled to an assembly or mechanism along with other gripper fingers that may be operable to control the gripper fingers for gripping the object.

The gripper unit may be used in a medical laboratory system for processing patient samples. In some embodiments, a gripper unit may be coupled to a robotic arm. Robotic arms may be used for the transportation of specimen containers in various areas of a laboratory system, such as input, distribution, centrifuge, decapper, aliquotter, output, sorting, recapping, and secondary tube lift areas. In some embodiments, robotic arms may be used to lift waste specimen containers from a specimen carrier using a gripper unit and discard them into a waste container.

Figure 1:
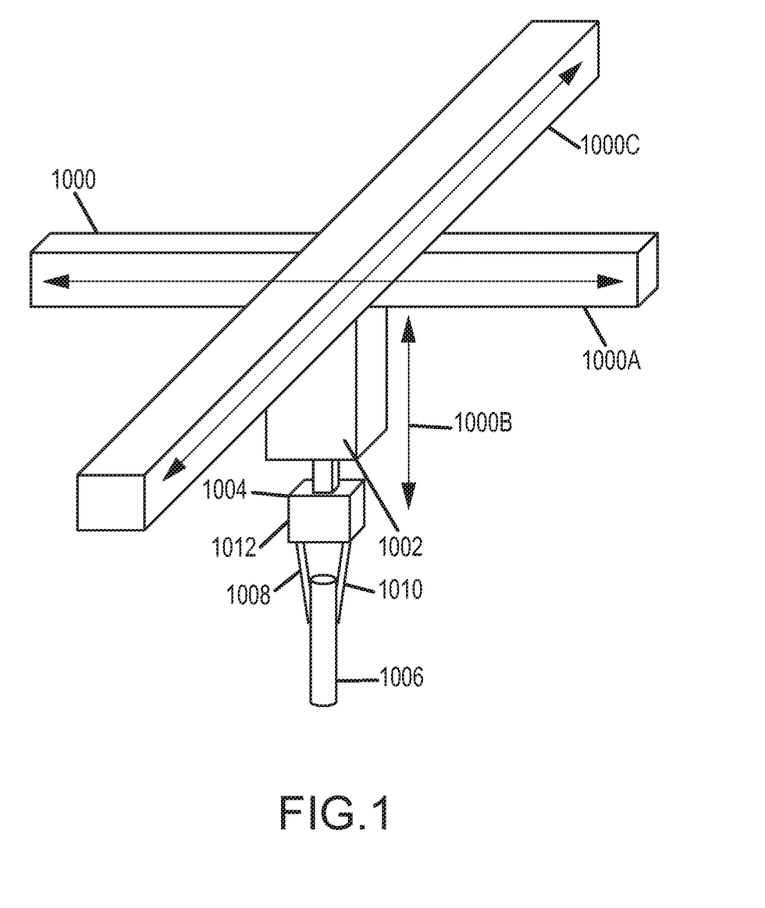
FIG. 1 depicts an example of a Cartesian or gantry robot with three independently moveable directions x-,y-, and z-.

The robotic arm architecture can differ in complexity dependent upon the given task. FIG. 1 depicts an example of a Cartesian or gantry robot 1000 with three independently moveable directions x-, y-, and z-. The gantry robot 1000 shown in FIG. 1 shows a simple robotic arm 1002 that can move up and down. More complex robotic arms may include, for example, a Selective Compliant Assembly Robot Arm (SCARA) or an articulated robotic arm with multiple joint arms.

In some embodiments of the invention, a gripper unit 1004, may be coupled to the robot arm 1002. The robot arm 1002 may be part of the gantry robot 1000 that is configured to move independently in three, orthogonal directions denoted as 1000A, 1000B and 1000C. As the gripper unit 1004 is transported by the robot arm 1002, the gripper unit 1004 may transport a specimen container 1006 held by the gripper unit 1004.

The gripper unit 1004 may have two or more moveable gripper fingers 1008, 1010 coupled to a body 1012 to grip the specimen container 1006. For example, the gripper fingers 1008, 1010 may move inwardly toward the specimen container 1006 until the specimen container 1006 is held in a fixed position between the gripper fingers 1008 and 1010. The gripper fingers 1008, 1010 may also be configured to spread outwardly to release the specimen container 1006. The robot arm 1002 may be part of a laboratory automation system, which is further described with reference to FIG. 3.

Figure 2A:
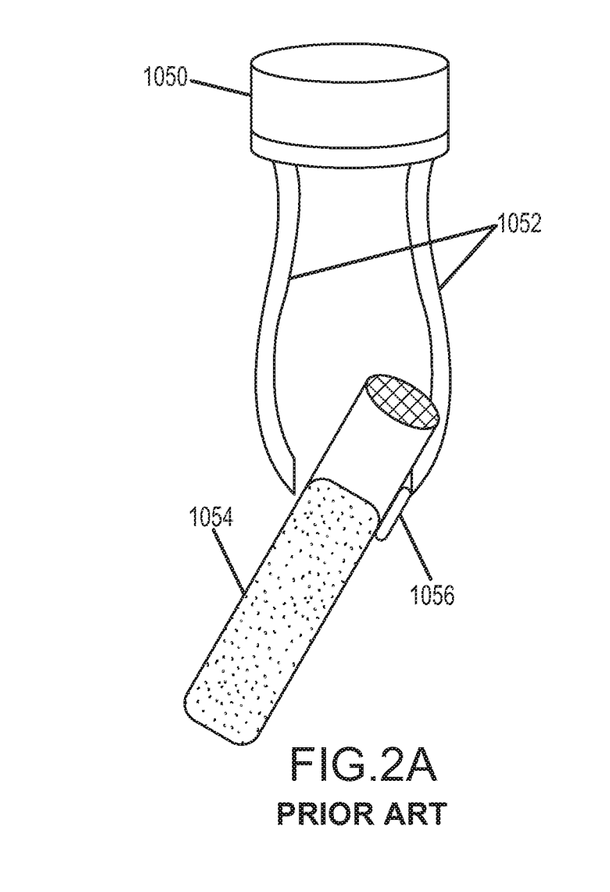
FIG. 2A illustrates a typical gripper unit operable to grip a specimen container.

FIG. 2A illustrates a typical gripper unit operable to grip a specimen container.

Typically, a gripper unit 1050 may be operable to grip a specimen container 1054 using gripper fingers 1052 to discard the specimen container 1054 into a waste container. The specimen container 1054 may be a test tube containing patient samples. Under normal conditions, the gripper unit 1050 may release the specimen container 1054 by opening the gripper fingers 1052. However, in some cases, a substance 1056 may be stuck to an outside surface of the specimen container 1054. The substance 1056 may be deposited due to contamination from aliquotting or glue from a label stuck on the surface of the specimen container 1054. Due to the presence of the substance 1056, the gripper fingers 1052 may get stuck to the specimen container 1054 during the process of discarding the specimen container 1054. As a result, when the gripper unit 1050 opens its gripper fingers 1052 to release the specimen container 1054, the specimen container 1054 may be left dangling because it is attached to the gripper finger. This may increase the processing time to discard the specimen containers as human intervention may be required to remove the stuck specimen container 1054. Further, contamination may be transported by the gripper fingers 1052 to other specimen containers, thus, further spreading the contamination.

Figure 2B:
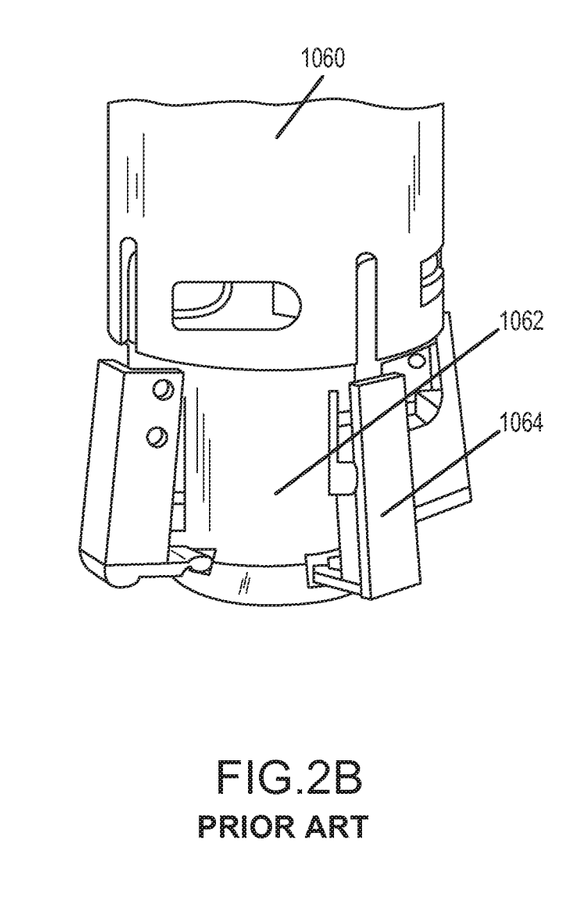
FIG. 2B illustrates a prior art robotic gripper that may be used as a strip-off element for caps.

FIG. 2B illustrates a prior art robotic gripper 1060 that may be used as a strip-off element for caps.

The robotic gripper 1060 comprises a strip-off element 1062 for caps using gripper fingers 1064. A similar robotic gripper is used in Beckman Automate™ 2500 series as a decapper for decapping or removing caps from specimen containers, such as, sample tubes. In such a system, if there is contamination on a sample tube, the contamination may be transferred to the body of the strip-off element 1060 (e.g., the cylinder). Since the strip-off element 1062 is attached to the body of the robotic gripper 1060, it may not be easily cleaned and the contamination may be transferred to other specimen containers. The presence of the strip off element 1062 on the body of the robotic gripper also makes it more difficult to see what is being gripped.

Embodiments of the invention provide an element that is detached from the gripper unit, thus, can be easily replaced or removed for cleaning, etc. The element may be part of a chute arrangement that can be mounted right above a waste container so the contamination does not get transferred to other components of the automation system. Embodiments may be used for any object that needs to be collected in a container, such as discarded specimen samples (e.g., waste tubes), secondary tubes that need not be stored, capillary waste, pipette tip waste or test tube cap waste used in various modules of a medical laboratory system (e.g., de and re-capper module, serum indices module, aliquoter module).

Figure 3:
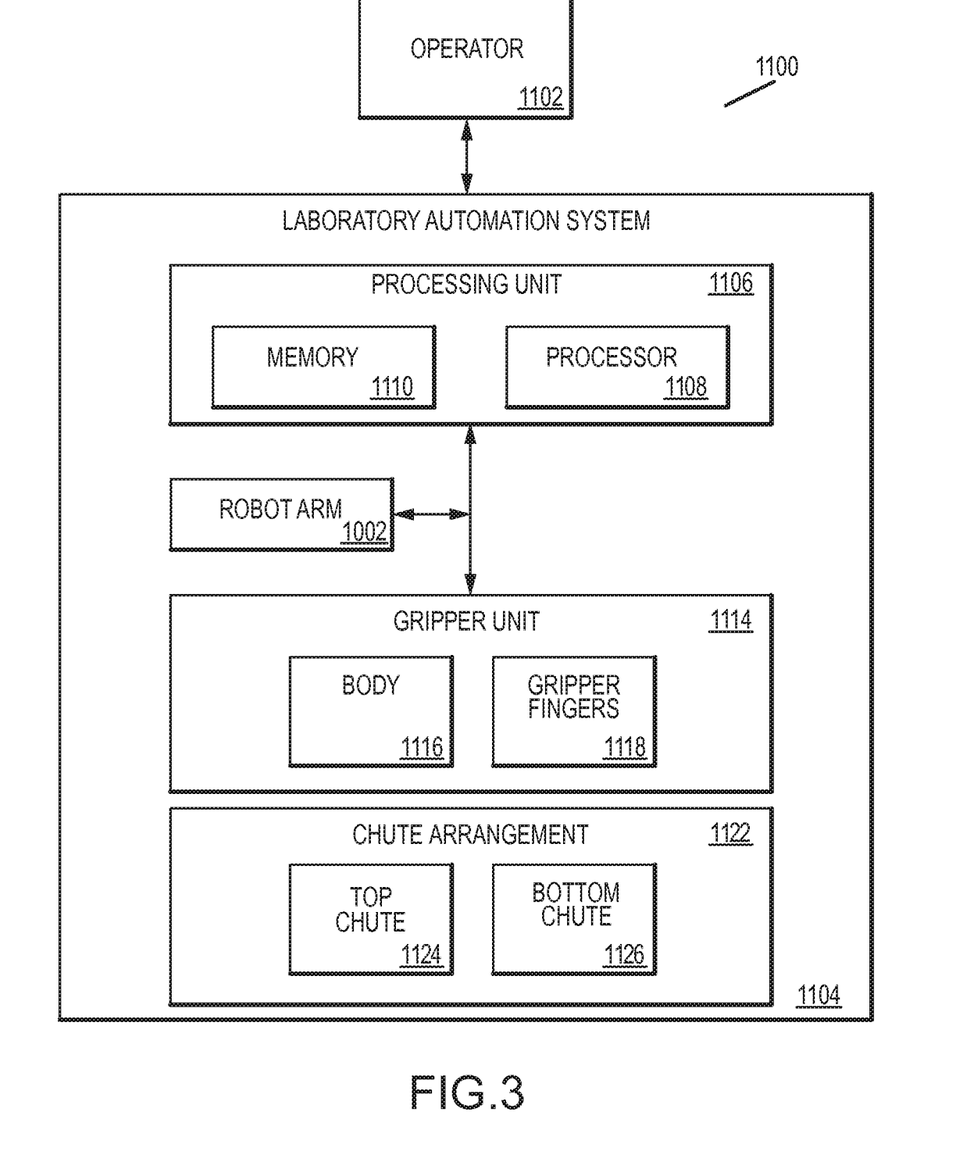
FIG. 3 illustrates a block diagram of a system that may be utilized in a laboratory.

FIG. 3 illustrates a block diagram of a system 1100 that may be utilized in a medical laboratory. The system 1100 may include an operator 1102 that may use a laboratory automation system 1104 to process samples (e.g., serum, plasma, gel, packed red blood cells, etc.). In the exemplary embodiment, the laboratory automation system 1104 includes the robot arm 1002, a processing unit 1106, a gripper unit 1114 and a chute arrangement 1122. However, a number of other units (not shown) may be utilized by the laboratory automation system 1104. For example, the laboratory automation system 1104 may include an input module, a distribution area, a centrifuge, a decapper, a serum indices measurement device, an aliquotter and an output/sorter in some embodiments of the invention. The robot arm 1002 may be part of the gantry robot 1000. The gripper unit 1114 may be configured to communicate with the processing unit 1106.

The processor 1108 may be configured to execute instructions or code in order to implement methods, processes or operations in various embodiments. In some embodiments, the processor may include other suitable processing elements (not shown), such as a microprocessor, a digital signal processor, a graphics processor, a co-processor, etc.

The memory 1110 may be coupled to the processor 1108 internally or externally (e.g., cloud based data storage) and may comprise any combination of volatile and/or non-volatile memory such as, for example, buffer memory, RAM, DRAM, ROM, flash, or any other suitable memory device. In some embodiments, the memory 1110 may be in the form of a computer readable medium (CRM), and may comprise code, executable by the processor 1108 for implementing methods described herein. In some embodiments, the processor 1108 may be part of a computer system as described with reference to FIG. 9.

The memory 1110 may also store other information. Such information may include types and dimensions of various specimen containers that may be collected in a waste container. The memory 1110 may also store information relating to a count of specimen containers that are dropped in the waste container through the chute arrangement 1122.

The laboratory automation system 1104 may utilize the robot arm 1002 to grip a specimen container (e.g., sample tube) using the gripper unit 1114. The gripper unit 1114 may include a body 1116 and gripper fingers 1118 that are coupled to the body 1116. It will be understood that the gripper unit 1114 may also include or interface with other units to enable the gripper unit perform the intended function.

In one embodiment, the gripper fingers 1118 are coupled to the body 1116. The body 1116 may be in the form of a support structure or a housing. It may have any suitable shape including a square or rectangular vertical or horizontal cross section. The gripper fingers 1118 can be capable of moving with respect to the body 1116. In one embodiment, the body 1116 may include one or more mounting structures so that the gripper fingers 1118 are coupled to the one or more mounting structures. It may also contain the well-known components (e.g., gears, solenoids, etc.) that allow the gripper unit to function. The body 1116 may be made of any suitable material including metal or plastic.

In one embodiment, the chute arrangement 1122 may include a top chute 1124 which may be in the form of an element implementing a strip-off feature and a bottom chute 1126 coupled to the top chute 1124. In some embodiments, the top chute 1124 may be coupled to the bottom chute 1126 using an adapter or a spacer unit for compatibility or height adjustments. In some embodiments, a sensor unit may be communicatively coupled to the chute arrangement 1122 that may be operable to detect a falling object passing through the chute arrangement 1122.

In embodiments of the invention, the robot arm 1002 may be operable to grip a specimen container (e.g., a sample tube) using the gripper unit 114 from a specimen carrier (e.g., a tube rack) and drop it through the chute arrangement 1122 into a waste container. This is further explained with reference to FIG. 4.

Figure 4:
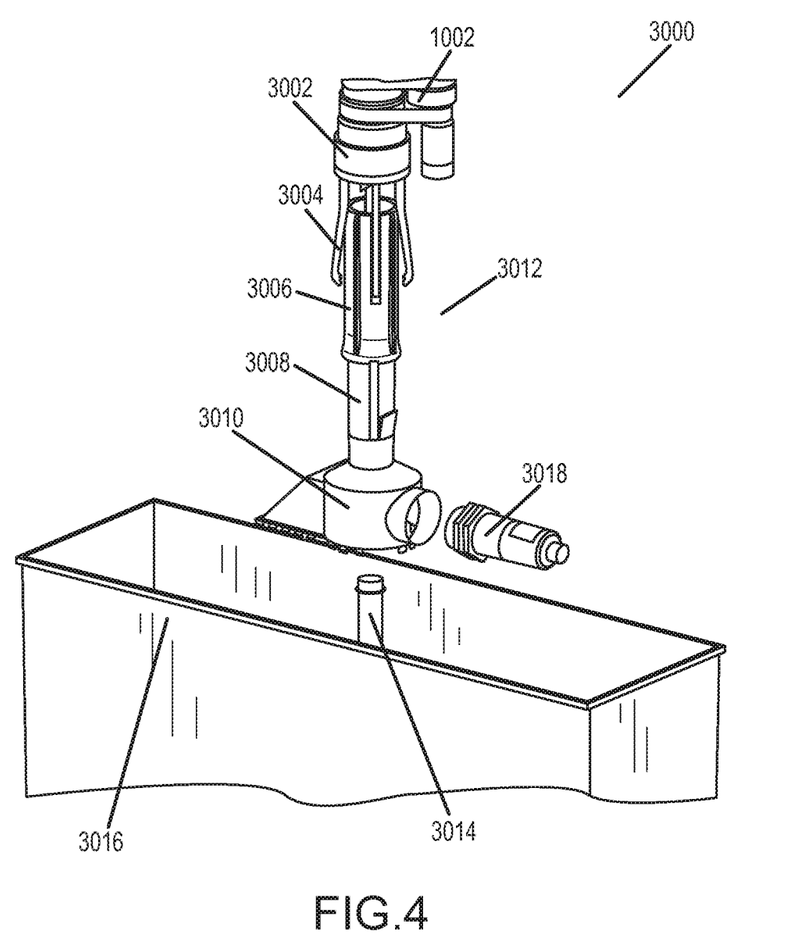
FIG. 4 illustrates certain elements of an exemplary system comprising a chute arrangement, in one embodiment of the invention.

FIG. 4 illustrates certain elements of an exemplary system 3000 comprising a chute arrangement, in one embodiment.

The exemplary system 3000 may include the robot arm 1002 coupled to a gripper unit 3002 including gripper fingers 3004. The gripper unit 3002 may grip specimen containers such as waste tubes, and the gripper fingers 3004 can automatically discard the specimen containers into a waste bin 3016. In one embodiment of the invention, a chute arrangement 3012 may include a top chute 3006 in the form of an element and a bottom chute 3010 coupled to the top chute 3006 through an optional adapter unit 3008. In one embodiment, the gripper unit 3002 may be communicatively coupled to the processing unit 1106. The processing unit 1106 may control the gripper unit 3002 using code stored in the memory 1110.

In some embodiments, an ultrasonic sensor unit 3018 may be in proximity to the chute arrangement 3012, as shown in FIG. 4. In some embodiments, the ultrasonic sensor unit 3018 may be configured as a transceiver for transmitting and detecting ultrasonic signals. The ultrasonic sensor unit 3018 may be configured to generate acoustic waves and to evaluate the waves reflected from a surface and received by the ultrasonic sensor unit 3018. In some embodiments, the ultrasonic sensor unit 3018 may be configured to detect an object, e.g., a specimen container 3014 passing through the chute arrangement 3012 by sending a signal through a side hole in the bottom chute 3010. In some embodiments, detection of a falling object through the chute arrangement 3012 may be used to keep a count of the number of objects (e.g., tubes, caps, etc.) that can be collected in the waste bin 3016. The operation of the ultrasonic sensor unit 3018 is explained in greater detail in a co-pending U.S. patent application Ser. No. 14/055,540, by Lukas Bearden, Andreas Donner-Rehm and Martin Muller, filed on the same day as the present application, and entitled "Container Fill Level Detection", the contents of which are incorporated by reference in its entirety for all purposes.

The gripper unit 3002 may be configured to grip the specimen container 3014 using the gripper fingers 3004. In embodiments of the invention, the chute arrangement 3012 helps direct the specimen container 3014 into the waste bin 3016, when the specimen container 3014 is released by the gripper fingers 3004. The chute arrangement 3012 may be configured to allow un-gripped objects to fall through the chute by means of gravity. If the specimen container 3014 is not sticky (i.e., no substance 1056), the specimen container 3014 may fall into the waste bin 3016 when it is released by the gripper fingers 3004. However, as explained above, the specimen container 3014 may stick to the gripper fingers 3004. In embodiments of the invention, the top chute 3006 can be an element and can separate the specimen container 3014 from the gripper fingers 3004, when the gripper fingers 3004 move outwardly to release the specimen container 3014. The top chute 3006 may restrain the specimen container 3014 from moving with the gripper fingers 3004 as they move outwardly away from the specimen container 3014. This allows the specimen container 3014 to separate from the gripper fingers 3004 so that it can pass down through the chute arrangement 3012.

The adapter unit 3008 may be configured as a spacer unit to provide a height adjustment for mounting the chute arrangement 3012 on a platform. One end of the adapter unit 3008 may be coupled to the top chute 3006 and another end of the adapter unit 3008 may be coupled to the bottom chute 3010.

The adapter unit 3008, in combination with the top chute 3006, may be configured to have a length that is equal to or greater than the length of the specimen container 3014 such that no part of the specimen container 3014 can stick to gripper fingers 3004 beyond the chute. In case a cap of the specimen container 3014 is partially or entirely removed from the specimen container 3014 before the specimen container 3014 is released from the gripper fingers 3004, a potential splash of the sample specimen (e.g., fluid) can be confined by the top chute 3006 and/or the adapter unit 3008. The chute arrangement 3012 may be able to accommodate specimen containers of any suitable length so that the specimen container does not interrupt the acoustic, light, or other signal used for detecting the falling specimen container, when the specimen container is in the grasp of the gripper unit 3002. In one embodiment, the combined length of the top chute 3006 and the adapter unit 3008 can be adjusted to accommodate lengths of different objects that are intended to be passing through the chute arrangement 3012.

The bottom chute 3010 may be configured to provide multiple functions. The bottom chute 3010 may include a mechanism for mounting on a platform to provide support or stability to the chute arrangement 3012. For example, one end of the bottom chute 3010 may comprise mounting tabs for mounting on a platform and another end of the bottom chute 3010 may couple to the adapter unit 3008 or directly to the top chute 3006. In one embodiment, the bottom chute 3010 may be configured to be in a close proximity of the ultrasonic sensor unit 3018 so that the ultrasonic sensor unit 3018 can detect a falling object passing through the bottom chute 3010. For example, an opening on the bottom chute 3010 may be in a line of sight of the ultrasonic sensor unit 3018 so that an ultrasonic signal transmitted by the ultrasonic sensor unit 3018 can reflect from a surface of an object passing through the bottom chute 3010 and bounce back to the ultrasonic sensor unit 3018. The ultrasonic sensor unit 3018 may be communicatively coupled to the processing unit 1106 so that a count of the falling objects can be stored and/or updated in the memory 1110. Although an ultrasonic sensor unit 3018 is shown and described, other types of sensor units such as optical sensor units and motion detectors may be used in other embodiments of the invention.

In FIG. 4, the bottom chute 3010 has wider dimensions than the top chute 3006. The increased size of the bottom chute 3010, in conjunction with the ultrasonic sensor unit 3018, can provide for the capability of detecting falling objects. However, it is to be noted that the bottom chute 3010 may have any suitable design as long as it can interface with the top chute 3006, with or without the adapter unit 3008.

In embodiments of the invention, the top chute 3006 enables the waste tube 3014 to strip off from the gripper fingers 3004, as further explained with reference to FIGS. 5A-5B.

Figure 5A:
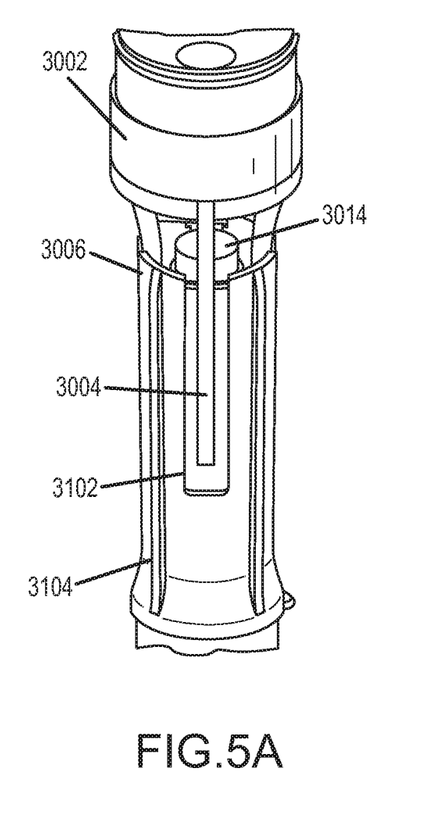
FIGS. 5A-5B illustrate close up views of a top chute comprising an element, in one embodiment of the invention.
Figure 5B:
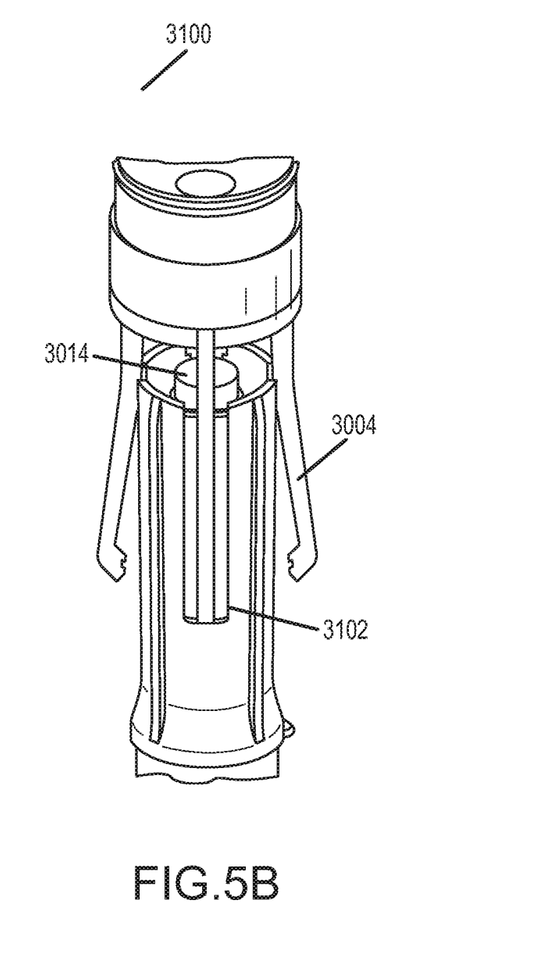

FIGS. 5A-5B are close up, perspective views of an arrangement 3100 of a top chute in form of an element.

As illustrated in FIG. 5A, the top chute 3006 includes a plurality of slots 3102. In one embodiment, each of the plurality of slots is parallel to a longitudinal axis of the top chute 3006. In embodiments of the invention, the gripper fingers 3004 may generally enter the plurality of slots 3102 from above for at least partially inserting the specimen container 3014 gripped by at least two of the gripper fingers 3004. In one embodiment, the gripper fingers 3004 may open laterally to release the gripped specimen container 3014. A geometric dimension of each of the plurality of slots 3102 may be smaller than an overall length, width or height of the specimen container 3014 such that the specimen container 3014 is unable to pass through the slots 3102 when released by the gripper fingers 3004. In one embodiment, the geometric dimension of each of the plurality of slots may be a width of the slot so that each of the gripper fingers 3004 may pass through the slot but not the object. Under normal conditions, the specimen container 3014 may drop down the chute arrangement 3012 into the waste bin 3016 when the specimen container 3014 is released from the gripper fingers 3004, as shown in FIG. 4. However, if there is contamination on the specimen container 3014, the specimen container 3014 may stick to the gripper fingers 3004. Embodiments provide a stripping feature in the top chute 3006 such that the gripper fingers 3004 can be moved by the gripper unit 3002 to extend outwardly through the slots 3102 so that the specimen container 3014 can be released and separated from the gripper fingers.

FIG. 5B illustrates open gripper fingers 3004 that have opened outwardly outside the slots 3102 of the top chute 3006. The gripper fingers 3004 do not touch the sample container 3014 and are completely separated from it.

The slots 3102 may be configured such that the gripper fingers 3004 may pass through the slots 3102. If the specimen container 3014 sticks to the gripper fingers 3004 due to some contamination during the movement of the opening of the gripper fingers 3004, the element of the top chute 3006 retains the specimen container 3014 within it so that the specimen container 3014 is released from the gripper fingers 3004 and passes down through the chute arrangement 3012. Because slots 3102 are smaller in dimensions (e.g., narrower) than the specimen container 3014, the specimen container 3014 does not pass through the slots 3102 when the gripper fingers 3004 pass through the slots and is restrained by the element. The element can be made of a material sufficiently strong to restrain the specimen container 3014 if the specimen container 3014 sticks to the gripper fingers 3004 due to contamination on the specimen container 3014. Some non-limiting examples of the material for the element are metal (e.g., steel or aluminum), plastic, Teflon, etc. Stabilizing bars 3104 on the surface of the top chute 3006 may help provide further stabilization.

The specimen container 3014 may be collected in a container, e.g., a container for waste collection or for further processing. The substance 1302 may get transported with the specimen container 1304 into the waste container instead of sticking to the gripper fingers 3004. This may avoid having contamination from the substance 1302 transferred to the other objects that may come in contact with the gripper fingers 3004.

Figure 6:
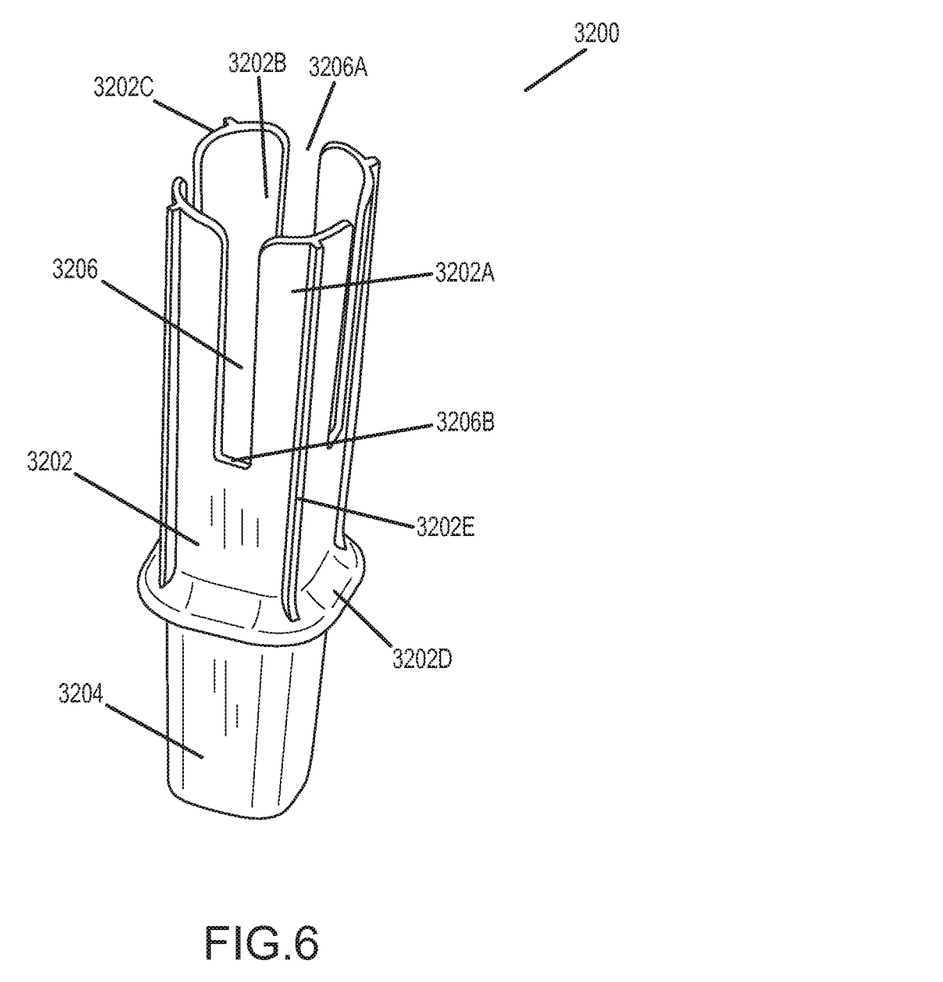
FIG. 6 illustrates a top chute arrangement with a square shaped profile, in one embodiment of the invention.

FIG. 6 illustrates a top chute arrangement with a square shaped radial cross-section, or a square shaped profile, according to one embodiment of the invention.

A top chute arrangement 3200 may comprise an element 3202 and an adapter unit 3204, both with a square shaped profile. The element 3202 may comprise an element body 3202A comprising a central axial bore 3202B, a first end 3202C and a second end 3202D. For example, the gripper unit 3002 may insert the specimen container 3014 held by the gripper fingers 3004 into the element 3202 from top for discarding it. In various embodiments of the invention, the element 3202 may be configured to have dimensions that may allow different types of objects (e.g., different types of tubes, caps, etc.) to be surrounded by the element body 3202A so that the element body 3202A can restrain the object when the object is released by the gripper fingers. The top chute arrangement 3200 may have any suitable profile that would allow a correct alignment of the element 3202 and the gripper unit 3002 to allow the gripper fingers 3004 to properly enter the plurality of slots 3206.

As shown in FIG. 6, the element body 3202A has a square shaped profile. In one embodiment, the element body 3202A may comprise four walls where each wall may comprise a slot. In some embodiments, the element body 3202A may comprise a plurality of stabilizing bars 3202E for providing stabilization or support to the element 3202. As illustrated in FIG. 6, there is one stabilizing bar on each side of the slot, which runs longitudinally along the element body 3202A from the first end 3202C to the second end 3202D.

In one embodiment, the second end 3202D of the element body 3202A may have slightly larger dimensions than the rest of the element body 3202A. In one embodiment, the second end 3202D may be configured to support the coupling of the stabilizing bars 3202E to the element body 3202 A. The stabilizing bars 3202 may be integrally formed with the main body of the element, or could be separate parts that are attached to the main body of the element. The second end 3202D may further be configured to couple to one end of the adapter unit 3204. The element body 3202A may comprise of a material with sufficient strength to restrain a specimen container from moving with the gripper fingers when the gripper fingers are moving away from the specimen container through the slots 3206. The number of slots 3206 may be same as the number of gripper fingers and configured in shape and size such that the gripper fingers may pass through the slots 3206 but the specimen container stays confined within the element 3202. In one embodiment, the slots 3206 are parallel to a longitudinal axis of the central axial bore 3202B.

In one embodiment, each slot in the plurality of slots 3206 may have a rectangular cross-section and may have an open end 3206A and a closed end 3206B. The open end 3206A may coincide with the first end 3202C of the element body 3202A to enable the gripper fingers to insert a gripped object into the central axial bore 3202B from above. The closed end 3206B may be at a distance approximately half way down the entire length of the element body 3202A. In some embodiments, the length and width of each slot may depend upon a number of factors such as the dimensions (e.g., length of the element, width of each wall, etc.) of the element body 3202, the dimensions (e.g., length, width, thickness, etc.) of the gripper finger passing through each slot, the dimensions of each object that may be surrounded by the element body 3202A for dropping through the top chute arrangement 3200, material of the element 3202, etc.

In one embodiment, the adapter unit 3204 has a square shaped profile. However, any suitable shape is possible. The square shaped profile of the adapter unit 3204 may provide for easy alignment with the element 3202. The adapter unit 3204 or other portion of the element 3202 having a square cross-sectional profile can be used to ensure that each time the top chute arrangement 3200 is installed, the plurality of slots 3206 are positioned to receive the gripper fingers. The square shaped profile of the element 3202 provides a benefit over a cylindrical shape since a cylindrical shaped chute may be rotated when replaced such that the gripper fingers are not aligned with the slots. In some embodiments, a cylindrical shape profile with specific alignment features may be used. In one embodiment, these features are preferably located at the second end 3202D of the element body 3202A and may e.g. interface with the adapter 3204 in such a way that an unintentional rotation or misplacement of the element 3202 that would lead to a mis-alignment of the slots 3206 in relation to the gripper fingers 3004, is avoided.

In one embodiment, the adapter unit 3204 is part of the element 3202. The adapter unit 3204 may further be configured to couple to a bottom chute for forming a chute arrangement that may be used to drop off waste objects into a waste container, e.g., the waste bin 3016. For example, referring back to FIG. 4, one end of the bottom chute 3010 which connects to the adapter unit 3008 may be configured to have a square shaped profile so that the bottom chute 3010 may be coupled to the adapter unit 3204 for forming a chute arrangement. Further, the chute arrangement may be coupled to a platform, as described with reference to FIG. 7.

Figure 7:
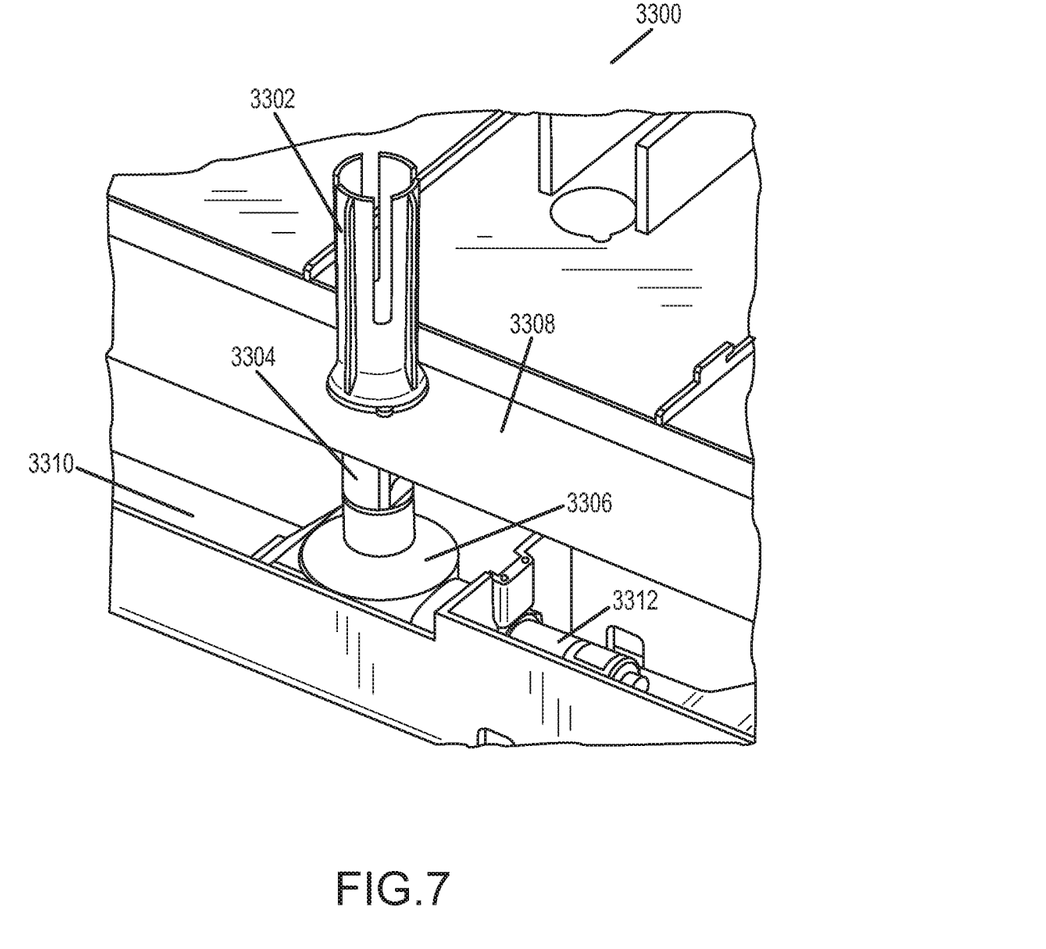
FIG. 7 illustrates a close up view of the placement of a chute arrangement, in one embodiment of the invention.

FIG. 7 illustrates a perspective view of the placement of a chute arrangement 3300 according to one embodiment of the invention.

As illustrated in FIG. 7, a top chute 3302 is coupled to a bottom chute 3306 via an adapter unit 3304. In one embodiment, the top chute 3302 may be attached directly to the bottom chute 3306 without the adapter unit 3304 or any other intermediary unit. In another embodiment, the adapter unit 3304 may be a part of the bottom chute 3306. Top chute 3302 may be easily removed or replaced for cleaning or other maintenance.

In one embodiment of the invention, the top chute 3302 may have a square shaped profile similar to the top chute 3202 of FIG. 6. Similarly, the adapter unit 3304 may have a square shaped profile similar to the adapter unit 3204 that provides an easy alignment with the top chute 3302. Further, the adapter unit 3304 or other portion of the top chute 3302 may be inserted into an opening, such as an opening in a deck 3308, for support or stability. The bottom chute 3306 may comprise a plurality of mounting tabs for mounting on a deckbase 3310. However, it is to be noted that any mechanism may be used to connect the bottom chute 3306 to the deckbase 3310 or any other stabilizing platform.

In one embodiment, the deck 3308 and the deckbase 3310 are part of the laboratory automation system 1104 (e.g., in a storage unit). In one embodiment, the deck 3308 may hold a plurality of specimen carrier racks holding a plurality of specimen carriers carrying multiple specimen containers.

In one embodiment, the adapter unit 3304 may be configured to compensate for the distance between the top chute 3302 and the bottom chute 3306 that results from the presence of the deck base 3310. In some embodiments, the bottom chute 3306 is in close proximity to an ultrasonic sensor 3312 such that the ultrasonic signals emitted from the ultrasonic sensor 3312 are directed towards an opening or side hole in the bottom chute 3306 to detect an object passing through the chute arrangement 3300. In one embodiment, an optical sensor may be used in place of the ultrasonic sensor unit 3312 for short range detection of the passing objects. The optical sensor may be mounted on the deck base 3310 such that an object falling through the chute arrangement 3300 is in its line of sight. The optical sensor may detect change in light when a sample container passes through the chute arrangement 3300. In some embodiments, the optical sensor may be implemented as a light barrier or a light curtain comprising multiple light barriers in parallel. The chute arrangement 3300 may be part of a specimen output system, as described with reference to FIG. 8.

Figure 8:
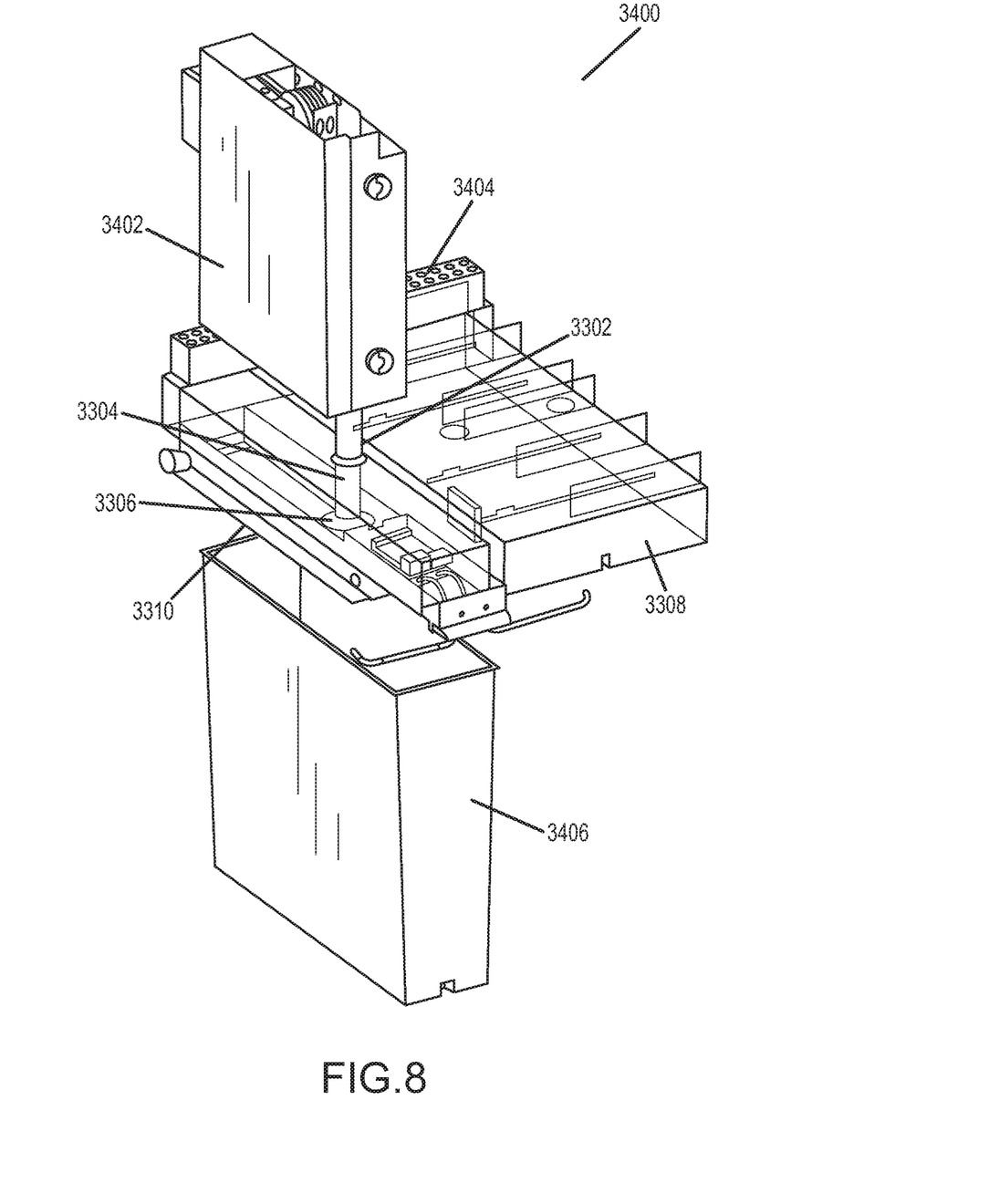
FIG. 8 illustrates overview of an exemplary specimen output system in one embodiment of the invention.

FIG. 8 illustrates overview of an exemplary specimen output system according to one embodiment of the invention.

In one embodiment, a specimen output system 3400 may be used in medical laboratory systems where specimen containers may need to be discarded, e.g., when the storage time for the specimen container has expired. The specimen container may be a test tube containing material for medical analysis, such as blood, serum, plasma, etc. An output robot 3402 may be used to transport the specimen containers from various areas of a laboratory system, such as input, distribution, centrifuge, decapper, aliquotter, output, analyzer, sorting, recapping, and secondary tube lift areas. The specimen containers may be stored in a single tube carrier rack 3404. A plurality of such racks may be placed in the deck 3308. The output robot 3402 may comprise a gripper unit (e.g., the gripper unit 3002) that may be used to automatically lift a tube from the single tube carrier rack 3404 for discarding into a waste bin 3406. Even though the exemplary system 3400 illustrates a test tube rack, specimen containers may be picked up from any handling system, such as a track system or via any test tube supply mechanism.

Embodiments may be used to help the specimen container pass through a chute arrangement into the waste bin 3406 when released by the gripper unit (not shown). In one embodiment, the chute arrangement includes one or more of the top chute 3302, adapter unit 3304 and the bottom chute 3306. The bottom chute 3306 may be mounted on the deckbase 3310 to provide support or stability (as shown in FIG. 7). The adapter unit 3304 may be configured to compensate for the distance between the top chute 3302 and the bottom chute 3306 caused by the deck base 3310.

Embodiments provide for a number of advantages. For example, by not attaching the waste bin 3406 to the chute arrangement or the deckbase 3310, the waste bin 3406 may be removed for emptying or replaced with another container.

In some embodiments, the specimen output system 3400 may be part of the laboratory automation system 1104. The output robot 3402 may utilize the robot arm 1002 for gripping an object using the gripper unit 1114 from the single tube carrier rack 3404 and dropping it into the waste bin 3406 through the chute arrangement comprising one or more of the top chute 3302, adapter unit 3304 and the bottom chute 3306. In one embodiment, the processing unit 1106 may be in communication with the output robot 3402 to control the output robot 3402 to start and stop the specimen container discarding process.

Figure 9:
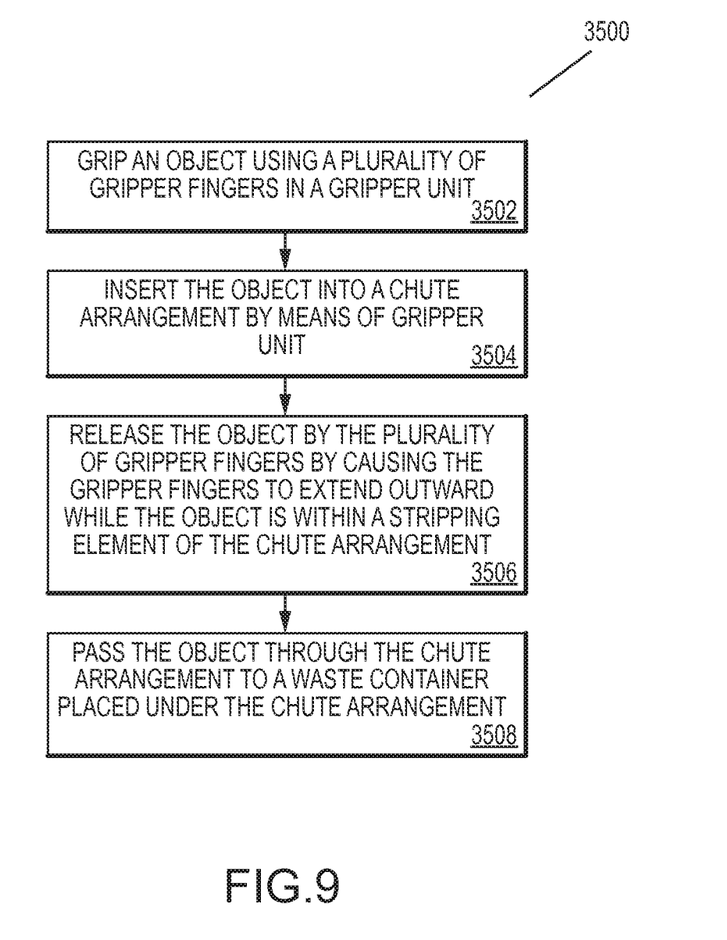
FIG. 9 illustrates a flow chart for a method of releasing an object through a chute arrangement, in one embodiment of the invention.

FIG. 9 illustrates a flow chart for a method of releasing an object through a chute arrangement, in one embodiment of the invention.

In step 3502, an object is gripped using a plurality of gripper fingers in a gripper unit. Referring back to FIG. 4, the gripper unit 3002 may grip the specimen container 3014 using the gripper fingers 3004 (e.g., from the single tube carrier rack 3404 as shown in FIG. 8) for discarding it into the waste bin 3016. The gripper unit 3002 may be part of the output robot 3402.

In step 3504, the object is inserted into a chute arrangement using the gripper unit. For example, the gripper unit 3002 may insert the specimen container 3014 into the chute arrangement 3012. The chute arrangement 3012 may comprise the top chute 3006 in the form of an element and the bottom chute 3010 coupled to the top chute 3006 through the optional adapter unit 3008. As shown in FIGS. 5A-5B, the specimen container 3014 may be inserted into the top chute 3006 from above by the gripper unit 3002 using the gripper fingers 3004. The gripper fingers 3004 may pass through the slots by entering the open ends of the slots in the top chute 3006 while holding the specimen container 3014.

In step 3506, the object is released by the plurality of gripper fingers by causing the gripper fingers to extend outward while the object is within an element of the chute arrangement. As shown in FIG. 5B, the specimen container 3014 may be released by the gripper fingers 3004 by causing the gripper fingers 3004 to extend outward while the specimen container 3014 is within the element 3006 of the chute arrangement 3012. In embodiments of the invention, the element 3006 helps separate the specimen container 3014 from the gripper fingers 3004, when the gripper fingers 3004 release the specimen container 3014 and pass through the plurality of slots 3102.

In step 3508, the object passes through the chute arrangement to a waste container placed under the chute arrangement. As shown in FIG. 4, the specimen container 3014 passes through the chute arrangement 3012 to the waste container 3016 when released by the gripper fingers 3004. The waste container 3016 is not attached to the chute arrangement 3012, thus can be easily replaced or emptied as needed.

Computer Architecture

The various participants and elements described herein with reference to FIG. 3 may operate one or more computer apparatuses to facilitate the functions described herein. Any of the elements in the above description, including any servers, processors, or databases, may use any suitable number of subsystems to facilitate the functions described herein, such as, e.g., functions for operating and/or controlling the functional units and modules of the laboratory automation system, transportation systems, the scheduler, the central controller, local controllers, etc.

Figure 10:
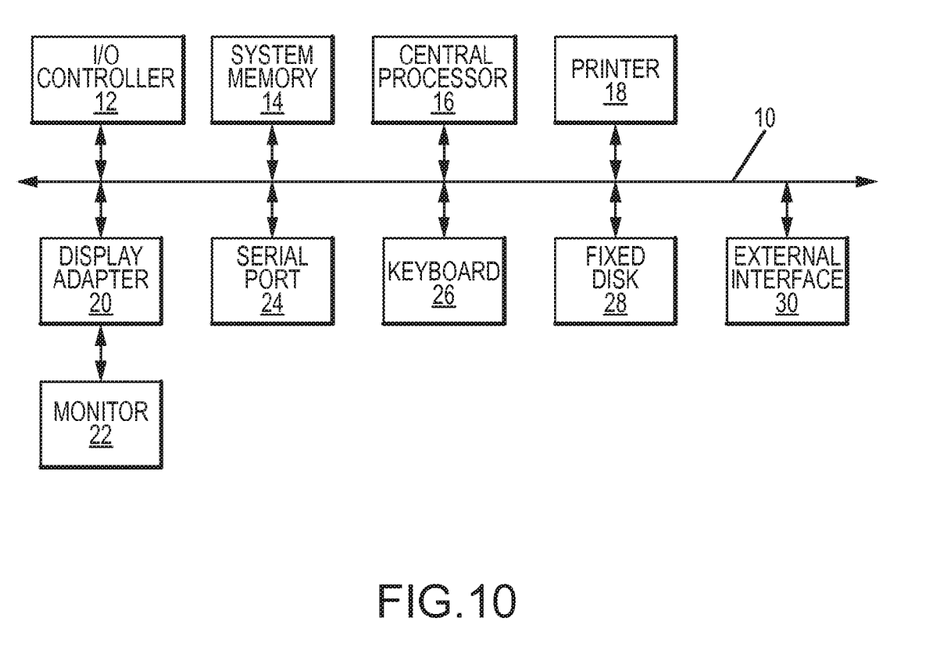
FIG. 10 illustrates a block diagram of an exemplary computer apparatus.

Examples of such subsystems or components are shown in FIG. 10. The subsystems shown in FIG. 10 are interconnected via a system bus 10. Additional subsystems such as a printer 18, keyboard 26, fixed disk 28 (or other memory comprising computer readable media), monitor 22, which is coupled to display adapter 20, and others are shown. Peripherals and input/output (I/O) devices, which couple to I/O controller 12 (which can be a processor or other suitable controller), can be connected to the computer system by any number of means known in the art, such as serial port 24. For example, serial port 24 or external interface 30 can be used to connect the computer apparatus to a wide area network such as the Internet, a mouse input device, or a scanner. The interconnection via system bus allows the central processor 16 to communicate with each subsystem and to control the execution of instructions from system memory 14 or the fixed disk 28, as well as the exchange of information between subsystems. The system memory 14 and/or the fixed disk 28 may embody a computer readable medium.

It should be understood that the present technology as described above can be implemented in the form of control logic using computer software (stored in a tangible physical medium) in a modular or integrated manner. Furthermore, the present technology may be implemented in the form and/or combination of any image processing. Based on the disclosure and teachings provided herein, a person of ordinary skill in the art will know and appreciate other ways and/or methods to implement the present technology using hardware and a combination of hardware and software Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

The above description is illustrative and is not restrictive. Many variations of the technology will become apparent to those skilled in the art upon review of the disclosure. The scope of the technology should, therefore, be determined not with reference to the above description, but instead should be determined with reference to the pending claims along with their full scope or equivalents.

One or more features from any embodiment may be combined with one or more features of any other embodiment without departing from the scope of the technology.

A recitation of "a", "an" or "the" is intended to mean "one or more" unless specifically indicated to the contrary.

All patents, patent applications, publications, and descriptions mentioned above are herein incorporated by reference in their entirety for all purposes. None is admitted to be prior art.

What is claimed is:

1. An element useful for releasing an object gripped by a gripper unit, wherein said gripper unit includes a plurality of gripper fingers for gripping the object, said element comprising:
   a tubular body comprising a central axial bore running the length of the tubular body with a first end and a second end, wherein the tubular body is configured to receive at least a portion of said object into said central axial bore through said first end, the first end including a plurality of slots parallel to the axis of the central axial bore and being open at the first end, said plurality of slots being positioned to receive portions of the plurality of gripper fingers of the gripper unit,
   wherein said tubular body is configured to restrain the object as the plurality of gripper fingers are extracted through the plurality of slots to release the object.

2. The element of claim 1, wherein a geometric dimension of each slot in the plurality of slots is smaller than an overall length, width or height of the object.

3. The element of claim 1, wherein the element has a square shaped profile.

4. The element of claim 1, wherein the plurality of slots includes exactly four slots.

5. The element of claim 1, wherein the second end is configured to couple to an adapter unit.

6. The element of claim 1, wherein the object is one of a sample test tube, a secondary test tube, a cap, a capillary, or a pipette.

7. A chute arrangement for guiding an object, the chute arrangement comprising:
   an element comprising a tubular body comprising a central axial bore, a first end and a second end opposite to the first end, the first end comprising a plurality of slots parallel to a longitudinal axis of the central axial bore;
   an adapter unit; and
   a bottom chute coupled to the element through the adapter unit, wherein one end of the adapter unit is coupled to the second end of the element and another end of the adapter unit is coupled to the bottom chute.

8. The chute arrangement of claim 7, wherein the element has an axial bore that has a larger volume than the object that is configured to pass through the element.

9. The chute arrangement of claim 7, wherein the bottom chute is configured to mount to a platform.

10. The chute arrangement of claim 7, wherein the element has a square shaped profile.

11. The chute arrangement of claim 7, wherein the adapter unit has a square shaped profile.

12. The chute arrangement of claim 7, wherein the combined length of the element and the adapter unit can accommodate the length of different objects that are intended to be passing through the chute arrangement.

13. A method of releasing an object through a chute arrangement, the method comprising:

gripping the object using a plurality of gripper fingers in a gripper unit;

inserting the object into the chute arrangement by means of the gripper unit, the chute arrangement comprising:

an element comprising an element body comprising a central axial bore, a first end and a second end, the first end comprising a plurality of slots; and releasing the object by the plurality of gripper fingers by causing the gripper fingers to extend outward through the plurality of slots while the object is within the element of the chute arrangement.

14. The method of claim 13, wherein the object is a specimen container.

15. The method of claim 13, further comprising:

passing the object through the chute arrangement to a waste container under the chute arrangement, the waste container not being attached to the chute arrangement.

16. The method of claim 13, wherein each of the slots is elongated.

17. The method of claim 13, wherein the chute arrangement further comprises:

an adapter unit; and a bottom chute coupled to the element through the adapter unit.

18. The method of claim 17, wherein the adapter unit is secured to a platform.

19. The method of claim 17, wherein a combined length of the element and the adapter unit is greater than a length of the object.

20. The method of claim 13, wherein the gripper unit is attached to an X, Y, Z robot.

* * * * *